US009631031B2

(12) United States Patent
Kadouche et al.

(10) Patent No.: US 9,631,031 B2
(45) Date of Patent: Apr. 25, 2017

(54) MULTISPECIFIC ANTIGENS BINDING FRAGMENTS AND MULTISPECIFIC ANTIBODIES DERIVED THEREFROM COMPRISING MUTANT CH1 AND CL-κ DOMAINS

(75) Inventors: Jean Kadouche, Paris (FR); Jean-Pierre Mach, Bellevue (CH); Olivier Michielin, Lausanne (CH); Vincent Zoete, Morges (CH); Justyna Iwaszkiewicz, Geneva (CH); Martine Cerutti, Saint-christol-lez-ales (FR); Sylvie Choblet, Ales (FR); Josee Golay, Bergamo (IT)

(73) Assignees: Centre National de la Recherche Scientifique, Paris (FR); Azienda Ospedaliera Papa Giovanni XXIII, Bergamo (IT); Universite de Lausanne, Lausanne (CH)

( * ) Notice: Subject to any disclaimer, the term of this patent is extended or adjusted under 35 U.S.C. 154(b) by 238 days.

(21) Appl. No.: 14/130,773

(22) PCT Filed: Jul. 6, 2012

(86) PCT No.: PCT/IB2012/053482
§ 371 (c)(1),
(2), (4) Date: Apr. 1, 2014

(87) PCT Pub. No.: WO2013/005194
PCT Pub. Date: Jan. 10, 2013

(65) Prior Publication Data
US 2014/0242076 A1    Aug. 28, 2014

(30) Foreign Application Priority Data
Jul. 7, 2011 (EP) .................................. 11305872

(51) Int. Cl.
*C07K 16/46* (2006.01)
*C07K 16/18* (2006.01)
*C07K 16/28* (2006.01)

(52) U.S. Cl.
CPC ........ *C07K 16/468* (2013.01); *C07K 16/2833* (2013.01); *C07K 16/2896* (2013.01); *C07K 2317/31* (2013.01); *C07K 2317/522* (2013.01); *C07K 2317/55* (2013.01); *C07K 2317/732* (2013.01)

(58) Field of Classification Search
None
See application file for complete search history.

(56) References Cited

U.S. PATENT DOCUMENTS

| | | | | |
|---|---|---|---|---|
| 5,959,083 A * | 9/1999 | Bosslet | ................. | C07K 16/30 424/130.1 |
| 2010/0081796 A1* | 4/2010 | Brinkmann | ........ | C07K 16/2863 530/387.3 |

FOREIGN PATENT DOCUMENTS

| | | |
|---|---|---|
| CN | 101952312 | 1/2011 |
| DE | 4419399 | 3/1995 |
| EP | 0826696 | 3/1998 |
| WO | 2007/147901 | 12/2007 |
| WO | 2009018386 | 2/2009 |
| WO | 2009/089004 | 7/2009 |
| WO | 2009/015518 | 12/2009 |
| WO | 2009/155513 | 12/2009 |
| WO | 2010/145793 | 12/2010 |
| WO | 2010/145895 | 12/2010 |

OTHER PUBLICATIONS

Paul, Fundamental Immunology, 3rd Edition, 1993, pp. 292-295.*
Bendig M. M. (Methods: A Companion to Methods in Enzymology, 1995; 8:83-93).*
Teerinen, Structure-Based Stability Engineering of the Mouse IgG1 Fab Fragment by Modifying Constant Domains, Journal of Molecular Biology, 361, pp. 687-697, 2006.
Marvin, Recombinant Approaches to IgG-Like Bispecific Antibodies, Acta Pharmacologica Sinica, 6, pp. 649-658, 2005.
Pluckthun, New Protein Engineering Approaches to Multivalent and Bisecific Antibody Fragments, Immunotechnology, 3, pp. 83-105, 1997.
Muller, The First Constant Domain (CH1 and CL) of an Antibody used as Heterodimerization Domain for Bispecific Minantibodies, FEBS Letters, 422, pp. 259-264, 1998.

* cited by examiner

*Primary Examiner* — Michael D Allen
(74) *Attorney, Agent, or Firm* — Morgan, Lewis & Bockius LLP

(57) ABSTRACT

The invention relates to multispecific antibody constructs comprising Fab fragments having mutations at the interface of the CH1 and CL domains, said mutations preventing heavy/light chain mispairing.

7 Claims, 7 Drawing Sheets

MULTISPECIFIC ANTIGENS BINDING FRAGMENTS AND MULTISPECIFIC ANTIBODIES DERIVED THEREFROM COMPRISING MUTANT CH1 AND CL-κ DOMAINS

The invention relates to the production of multispecific, in particular bispecific, antibody molecules.

Among protein-based drugs, monoclonal antibodies (mAbs) have a particular characteristic, acting both as a drug and as a targeted delivery system. Mabs have recently shown a great potential in treatment of various diseases, including in particular several types of cancer, where they are much more specific than conventional chemotherapy.

The basic structure of a naturally occurring antibody molecule is a Y-shaped tetrameric quaternary structure consisting of two identical heavy chains and two identical light chains, held together by non-covalent interactions and by inter-chain disulfide bonds.

In mammalian species, there are five types of heavy chains: α, δ, ε, γ, and μ, which determine the class (isotype) of immunoglobulin: IgA, IgD, IgE, IgG, and IgM, respectively. The heavy chain N-terminal variable domain (VH) is followed by a constant region, containing three domains (numbered CH1, CH2, and CH3 from the N-terminus to the C-terminus) in heavy chains γ, α and δ, while the constant region of heavy chains μ and ε is composed of four domains (numbered CH1, CH2, CH3 and CH4 from the N-terminus to the C-terminus). The CH1 and CH2 domains of IgA, IgG, and IgD are separated by a flexible hinge, which varies in length between the different classes and in the case of IgA and IgG, between the different subtypes: IgG1, IgG2, IgG3, and IgG4 have respectively hinges of 15, 12, 62 (or 77), and 12 amino acids, and IgA1 and IgA2 have respectively hinges of 20 and 7 amino acids.

There are two types of light chains: λ and κ, which can associate with any of the heavy chains isotypes, but are both of the same type in a given antibody molecule. Both light chains appear to be functionally identical. Their N-terminal variable domain (VL) is followed by a constant region consisting of a single domain termed CL.

The heavy and light chains pair by protein/protein interactions between the CH1 and CL domains, and the two heavy chains associate by protein/protein interactions between their CH3 domains. The structure of the immunoglobulin molecule is generally stabilised by interchains disulfide bonds between the CH1 and CL domains and between the hinges.

The clinical efficacy of therapeutic antibodies relies on both their antigen-binding function and their effector functions, which are respectively associated with different parts of the immunoglobulin molecule.

The antigen-binding regions correspond to the arms of the Y-shaped structure, which consist each of the complete light chain paired with the VH and CH1 domains of the heavy chain, and are called the Fab fragments (for Fragment antigen binding). Fab fragments were first generated from native immunoglobulin molecules by papain digestion which cleaves the antibody molecule in the hinge region, on the amino-terminal side of the interchains disulfide bonds, thus releasing two identical antigen-binding arms. Other proteases such as pepsin, also cleave the antibody molecule in the hinge region, but on the carboxy-terminal side of the interchains disulfide bonds, releasing fragments consisting of two identical Fab fragments and remaining linked through disulfide bonds; reduction of disulfide bonds in the F(ab')2 fragments generates Fab' fragments.

The part of the antigen binding region corresponding to the VH and VL domains is called the Fv fragment (for Fragment variable); it contains the CDRs (complementarity determining regions), which form the antigen-binding site (also termed paratope). Besides allowing to direct specifically the antibody to its goal, the antigen-binding region may induce upon binding to its target antigen a variety of biological signals, which may be positive or negative depending on both the targeted antigen and the epitope recognised by the antibody on said antigen. For use in the field of cancer therapy, one generally favours antibodies delivering a growth-inhibitory or a pro-apoptotic signal, resulting in cytostasis or in death of the tumor cells (VERMA et al., J Immunol, 186, 3265-76; 2011).

The effector function of the antibody results from its binding to effector molecules such as complement proteins, or to Fc receptors on the surface of immune cells such as macrophages or natural killer (NK) cells. It results in different effects leading to the phagocytosis or lysis of the targeted antigen, such as antibody dependent phagocytosis (ADP), antibody-dependent cell mediated cytotoxicity (ADCC), or complement dependent cell mediated cytotoxicity (CDC).

The effector region of the antibody which is responsible of its binding to effector molecules or cells, corresponds to the stem of the Y-shaped structure, and contains the paired CH2 and CH3 domains of the heavy chain (or the CH2, CH3 and CH4 domains, depending on the class of antibody), and is called the Fc (for Fragment crystallisable) region.

The ADCC, ADP, and CDC mediated by the Fc region play a major part in the therapeutic activity of mAbs. The ADCC mechanism seems to be central, since it has been demonstrated that in nude mice genetically deficient for the Fc gamma receptor, the therapeutic action against human tumour xenografts of the two major clinically successful mAbs, anti-HER2 and anti-CD20, was almost entirely abolished (CLYNES et al., Nat Med, 6, 443-6, 2000). The ADP mechanism has also been shown to be of central importance in several murine models of human tumors (UCHIDA et al., J. Exp. Med. 199: 1659-69, 2004), and CDC has also been demonstrated to play a fundamental role in the therapeutic activity of anti-CD20 in vivo (DI GAETANO et al., J Immunol, 171, 1581-7, 2003).

Due to the identity of the two heavy chains and the two light chains, naturally occurring antibody molecules have two identical antigen-binding sites and thus bind simultaneously to two identical epitopes.

In the 1980s, bispecific antibodies having on a same molecule two antigen-binding sites recognizing two different epitopes and therefore capable of simultaneous binding to two different targets, were generated by fusing two cells producing antibodies with distinct specificities (MILSTEIN & CUELLO, Nature, 305, 537-40, 1983). It was shown that such bi-specific antibodies were able to target effector T cells toward tumor cells (STAERZ et al., Nature, 314, 628-31, 1985).

A wide range of applications for bi-specific antibodies has been described (SONGSIVILAI & LACHMANN, Clin Exp Immunol, 79, 315-21, 1990), including for instance, in the therapeutic field, targeting of effector cells (cytotoxic T cells, NK cells, and macrophages), or of effector molecules (toxins, drugs, prodrugs, cytokines, radioisotopes, and complement system) and in the diagnostic field, use as reagents in immunoassays.

Initially, bi-specific antibodies have been prepared by chemical conjugation, or by use of quadromas resulting from the fusion between two hybridoma cell lines producing two different Mabs. However, chemical conjugation may occasionally alter the antigen binding sites, resulting in an impairment of the biological properties of the antibody. The quadroma approach has the drawback that the random pairing of heavy and light chains from two different antibodies leads theoretically to ten equally possible combinations resulting in a mixture of immunoglobulin molecules, only one of which is the desired bi-specific product, which has to be separated from the mispaired products.

More recently, genetic engineering has become the method of choice to produce bi-specific antibodies and had led to the development of a wide variety of different recombinant bi-specific antibody formats. Some of these bi-specific antibodies are very simple and derive from single-chain Fv (scFv) fragments from two (or more) different antibodies, associated through an appropriate peptide linker. These antibodies are relatively easy to produce, and since they are formed by a single polypeptide chain and contain only the Fv regions of the parent antibodies, there is no problem of mispairing between chains. However they are smaller than full-length immunoglobulins, and are devoid of constant regions, in particular of the Fc region. Although it may be advantageous in some applications, for instance when one wishes to avoid Fc-mediated effects, it is a disadvantage when Fc-mediated effector function such as CDC, ADCC or ADP is desired. Also, due to their small size and lack of Fc region, they have a very short half-life in vivo.

Therefore, other bi-specific recombinant antibodies formats, mimicking more closely the naturally occurring immunoglobulin molecule, and in particular having a full Fc region, have been designed. They can be grouped into two main formats.

In the first one (IgG scFv), scFv fragments from an antibody A are fused to the ends (generally the C-terminal ends) of the heavy chains of an antibody B. The resulting antibody having only one type of heavy chain, which contains the VH, CH1, CH2 and CH3 domains of antibody B and the VH and VL domains of antibody A, and one type of light chain which contains the VL and CL domains of antibody B, mispairing between chains does not occur. Such a format is described for instance by QU et al. (Blood, 111, 2211-9, 2008).

In the second one, the heavy chain and the light chain from an antibody A are paired with the heavy chain and the light chain from an antibody B. This format reproduces the bi-specific antibodies produced by the quadromas, and therefore raises similar problems of mispairing. To solve the problem of mispairing of the heavy chains, it has been proposed to mutate the CH3 domains of the antibodies in order to favour their heterodimerization (i.e. pairing of heavy chain A with heavy chain B) and to prevent their homodimerization. This was done by the so-called "knob into holes" approach (RIDGWAY et al., Protein Eng, 9, 617-21, 1996; U.S. Pat. No. 7,695,936). A "knob" mutation consisting in the replacement of a small amino-acid by a larger one is introduced at the CH3 dimer interface of the heavy chain of antibody A, resulting in a steric hindrance which prevents homodimerization. Concurrently in order to promote heterodimerization, a complementary "hole" mutation consisting in the replacement of a large amino-acid by a smaller one is introduced into the CH3 domain of antibody B. To solve the problem of the heavy chain/light chain mispairing, it has been proposed to use antibodies of different specificities but sharing a common light chain, previously identified from an scFv phage library (MERCHANT et al., Nat Biotechnol, 16, 677-81, 1998; U.S. Pat. No. 7,183,076). The drawback of this approach is the difficulty in identifying antibodies having a common light chain.

The inventors have now found that by mutating some key residues at the interface of the CH1 and CL domains, it is possible to prevent heavy chain/light chain mispairing and thus to ensure the desired matching of the chains.

They have more specifically found several sets of mutations suitable to this end. In a first one, a pair of interacting polar interface residues is exchanged for a pair of neutral and salt bridge forming residues. The replacement of Thr192 by a Glu on CH1 chain and exchange of Asn137 to a Lys on CL chain was selected. These two mutated residues form a salt bridge, which is presumed to reinforce the specificity of the association, whereas an unwanted pairing should be avoided by the lack of sterical and charge complementarity between the wild type and variant chains. Additionally a substitution of Ser114 to Ala on CL chain was made to avoid steric clashes with a bigger lysine side chain.

In a second set of mutations the inventors chose to replace the Leu143 of the CH1 domain by a Gln residue, while the facing residue of the CL chain, that is Val133, was replaced by a Thr residue. This first double mutation constitutes the switch from hydrophobic to polar interactions. Simultaneously a mutation of two interacting serines (Ser188 on CH1 chain and Ser176 on CL chain) to valine residues was selected to perform the switch from polar to hydrophobic interactions. This exchange of the polar/hydrophobic character of the interface interactions is expected to keep the affinity between the mutated CL and CH1 domains unchanged, while decreasing their respective affinity for other wild type counterparts, thus preventing mispairing by virtue of unfavorable interactions occurring upon mismatched (variant/wild type) chains complexation a pair of interacting apolar residues is exchanged for a pair of polar amino acids, while a pair of interacting polar residues is simultaneously exchanged for a pair of hydrophobic residues.

The third and fourth set of mutations are "knob into holes" mutations. More specifically, in the third set of mutations (KH1) the Leu124 and Leu143 of the CH1 domain have been respectively replaced by an Ala and a Glu residue while the Val133 of the CL chain has been replaced by a Trp residue, and in the fourth set of mutations (KH2), the Val190 of the CH1 domain has been replaced by an Ala residue, and the Leu135 and Asn137 of the CL chain have respectively been replaced by a Trp and an Ala residue.

Sequence position numbers used herein for the CH1 and CL domains refer to Kabat numbering (Kabat, E. A. et al., Sequences of proteins of immunological interest. 5th Edition—US Department of Health and Human Services, NIH publication n° 91-3242, pp 662,680,689, 1991).

An object of the present invention is therefore a mutated Fab fragment selected among:
  a) a Fab fragment consisting of:
  the VH and VL domains of an antibody of interest;
  a CH1 domain which is derived from the CH1 domain of an immunoglobulin by substitution of the threonine residue at position 192 of said CH1 domain with a glutamic acid residue; and
  a CL domain which is derived from the CL domain of an immunoglobulin by substitution of the asparagine residue at position 137 of said CL domain with a lysine residue and substitution of the serine residue at position 114 of said CL domain with an alanine residue;

b) a Fab fragment consisting of:
the VH and VL domains of an antibody of interest;
a CH1 domain which is derived from the CH1 domain of an immunoglobulin by substitution of the leucine residue at position 143 of said CH1 domain with a glutamine residue and substitution of the serine residue at position 188 of said CH1 domain with a valine residue; and
a CL domain which is derived from the CL domain of an immunoglobulin by substitution of the valine residue at position 133 of said CL domain with a threonine residue and substitution of the serine residue at position 176 of said CL domain with an valine residue.
c) a Fab fragment consisting of:
the VH and VL domains of an antibody of interest;
a CH1 domain which is derived from the CH1 domain of an IgG immunoglobulin by substitution of the leucine residue at position 124 of said CH1 domain with an alanine residue and substitution of the leucine residue at position 143 of said CH1 domain with a glutamic acid residue;
a CL domain which is derived from the CL domain of an IgG immunoglobulin by substitution of the valine residue at position 133 of said CL domain with a tryptophane residue;
d) a Fab fragment consisting of:
the VH and VL domains of an antibody of interest;
a CH1 domain which is derived from the CH1 domain of an immunoglobulin by substitution of the valine residue at position 190 of said CH1 domain with an alanine residue; and
a CL domain which is derived from the CL domain of an immunoglobulin by substitution of the leucine residue at position 135 of said CL domain with a tryptophane residue, and substitution of the asparagine residue at position 137 of said CL domain with an alanine residue.

According to a preferred embodiment, the CH1 domain is derived from a IgG immunoglobulin, advantageously of the IgG1 subtype. The CL domain is preferably a kappa type. Preferably, for use in human therapy, the immunoglobulin from which the mutated CH1 and CL domains are derived is a human immunoglobulin.

The VH and VL domains can be derived from any antibody, native or genetically engineered, recognizing an epitope that one wishes to target.

The mutated Fab fragments of the invention can be used in any multispecific antibody construct where it is necessary to prevent heavy chain/light chain mispairing.

Advantageously, they are used in a new multispecific antibody construct designed by the inventors, comprising one or more multispecific antigens-binding fragment(s) each of which consists essentially of tandemly arranged Fab fragments, separated by appropriate linkers.

An "antigens-binding fragment" is defined herein as a molecule having two or more antigen-binding regions, each recognizing a different epitope. The different epitopes can be borne by a same antigenic molecule or by different antigenic molecules.

Therefore, another object of the invention is a multispecific antigens-binding fragment, comprising at least two, and up to five, different Fab fragments selected among:
a Fab fragment (herein also defined as a: "wild-type Fab fragment") comprising wild-type CH1 and CL domains of an immunoglobulin
a mutated Fab fragment (a) as defined above;
a mutated Fab fragment (b) as defined above;
a mutated Fab fragment (c) as defined above;
a mutated Fab fragment (d) as defined above;

each Fab fragment recognizing a different epitope of interest and said Fab fragments being tandemly arranged in any order, the C-terminal end of the CH1 domain of a first Fab fragment being linked to the N-terminal end of the VH domain of the following Fab fragment through a polypeptide linker. Generally, said polypeptide linker should have a length of at least 20, preferably at least 25, and still more preferably at least 30, and up to 80, preferably up to 60, and still more preferably up to 40 amino-acids.

Advantageously, said polypeptide linker comprises all or part of the sequence of the hinge region of one or more immunoglobulin(s) selected among IgA, IgG, and IgD. If the antibody is to be used in human therapy, hinge sequences of human origin will be preferred.

Sequences of the hinge regions of human IgG, IgA and IgD are indicated below:

IgA1 (SEQ ID NO: 1):
VPSTPPTPSPSTPPTPSPS

IgA2 (SEQ ID NO: 2):
VPPPPP

IgD (SEQ ID NO: 3):
ESPKAQASSVPTAQPQAEGSLAKATTAPATTRNTGRGGEEKKKEKEKEE

QEERETKTP

IgG1 (SEQ ID NO: 4):
EPKSCDKTKTCPPCP

IgG2 (SEQ ID NO: 5):
ERKCCVECPPCP

IgG3:
(SEQ ID NO: 6)
ELKTPLGDTTHTCPRCP
followed by 0 or 1 to 4 repeats of (SEQ ID NO: 7)
EPKSCDTPPPCPRCP.

IgG4:
(SEQ ID NO: 8)
ESKYGPPCPSCP

Said polypeptide linker may comprise all or part of the sequence of the hinge region of only one immunoglobulin. In this case, said immunoglobulin may belong to the same isotype and subclass as the immunoglobulin from which the adjacent CH1 domain is derived, or to a different isotype or subclass.

Alternatively, said polypeptide linker may comprise all or part of the sequences of hinge regions of at least two immunoglobulins of different isotypes or subclasses. In this case, the N-terminal portion of the polypeptide linker, which directly follows the CH1 domain, preferably consists of all or part of the hinge region of an immunoglobulin belonging to the same isotype and subclass as the immunoglobulin from which said CH1 domain is derived.

Optionally, said polypeptide linker may further comprise a sequence of from 2 to 15, preferably of from 5 to 10 N-terminal amino-acids of the CH2 domain of an immunoglobulin.

In some cases, sequences from native hinge regions can be used; in other cases point mutations can be brought to these sequences, in particular the replacement of one or more cysteine residues in native IgG1, IgG2 or IgG3 hinge sequences by alanine or serine, in order to avoid unwanted intra-chain or inter-chains disulfide bonds.

A non-limitative example of a polypeptide linker which can be used in a multispecific antigens-binding fragment of the invention is a polypeptide having the following sequence: EPKSCDKTHTCPPCPAPELLGGPSTPPTPSPSGG (SEQ ID NO: 9). Said polypeptide consists of the full length sequence of human IgG1 hinge (SEQ ID NO: 4), followed by the 9 N-terminal amino-acids of human IgG1 CH2 (APELLGGPS, SEQ ID NO: 10), by a portion of the sequence of human IgA1 hinge (TPPTPSPS, SEQ ID NO: 11), and by the dipeptide GG, added to provide supplemental flexibility to the linker.

Optionally, a shorter portion of the N-terminal sequence of the human IgG1 CH2 domain can be used. Also, a longer portion of human IgA1 hinge, up to its full-length sequence (preferably minus the N-terminal valine residue) can be used. According to a particular embodiment, said human IgA1 hinge sequence can be replaced by an artificial sequence, containing an alternation of threonine, serine and proline residues.

For instance, a variant of the polypeptide of SEQ ID NO: 9, which is also suitable for use in a multispecific antigens-binding fragment of the invention is a polypeptide having the following sequence: EPKSCDKTHTCPPCPAPELLPSTPPSPSTPGG (SEQ ID NO: 12). In this polypeptide, the full length sequence of human IgG1 hinge is followed by the 5 N-terminal amino-acids of human IgG1 CH2 (APELL, SEQ ID NO: 13), and by the sequence PSTPPSPSTP (SEQ ID NO: 14).

In case of a multispecific antigens-binding fragment of the invention, comprising more than two different Fab fragments, the polypeptide linkers separating the Fab fragments can be identical or different.

According to a preferred embodiment of a multispecific antibody of the invention, it has two identical antigens-binding arms, each consisting of a multispecific antigens-binding fragment as defined above. The antigens-binding arms can be linked together in diverse ways, depending on the intended use for the antibody.

If one wishes to obtain an antibody without Fc-mediated effects, the antibody will comprise no Fc region. In this case, the two antigens-binding arms can be linked together for instance:
- by homodimerization of the antigens-binding arms through the inter-chain disulfide bonds provided by the polypeptide linker(s) separating the Fab fragments if said linker contain cystein residues; and/or
- through the addition at the C-terminal end of each antigens-binding arm, of a polypeptide extension containing cystein residues allowing the formation of inter-chain disulfide bonds, and homodimerization of said polypeptide extension resulting in a hinge-like structure; by way on non-limitative examples, said polypeptide extension may be for instance a hinge sequence of an IgG1, IgG2 or IgG3;
- through a semi-rigid linker joining the C-terminal ends of the heavy chains of the two antigens-binding arms to form a single polypeptide chain and maintaining said antigens-binding arms at a sufficient distance between each other Alternatively, if effector functions such as CDC, ADCC or ADP are desired, a multispecific antibody of the invention will further comprise a Fc domain providing these effector functions. The choice of the Fc domain will depend on the type of effector functions which are desired.

In this case, a multispecific antibody of the invention has an immunoglobulin-like structure, comprising:

- two identical multispecific antigens-binding arms as defined above;
- the dimerized CH2 and CH3 domains of an immunoglobulin;
- either the hinge region of an IgA, IgG, or IgD, linking the C-terminal ends of the CH1 domains of the antigens-binding arms to the N-terminal ends of the CH2 domains, or alternatively, the CH4 domains of an IgM or IgE following the CH3 domains, the C-terminal ends of the CH1 domains of the antigens-binding arms being in this case linked directly to the N-terminal ends of the CH2 domains.

Preferably, the CH2 and CH3 domains and either the hinge region or the CH4 domains are derived from a same immunoglobulin or from immunoglobulins of the same isotype and subclass as the CH1 domains of the antigens binding arm.

The CH2, CH3, and eventually CH4 domains, as well as the hinge regions from native immunoglobulins can be used. It is also possible to mutate them, if desired, for instance in order to modulate the effector function of the antibody. In some instances, whole or part of the CH2 or the CH3 domain can be omitted.

The invention also encompasses any protein chain selected among:
- a light chain of a mutated Fab fragment of the invention;
- a heavy chain of a mutated Fab fragment of the invention;
- a heavy chain of an antigens-binding fragment of the invention;
- a heavy chain of an immunoglobulin-like multispecific antibody of the invention.

Another object of the invention is a polynucleotide comprising a sequence encoding a protein chain of the invention. Said polynucleotide may also comprise additional sequences: in particular it may advantageously comprise a sequence encoding a leader sequence or signal peptide allowing secretion of said protein chain.

The present invention also encompasses recombinant vectors, in particular expression vectors, comprising a polynucleotide of the invention, associated with transcription- and translation-controlling elements which are active in the host cell chosen. Vectors which can be used to construct expression vectors in accordance with the invention are known in themselves, and will be chosen in particular as a function of the host cell one intends to use.

The present invention also encompasses host-cells transformed with a polynucleotide of the invention. Preferably, said host cell is transformed with a polynucleotide encoding a heavy chain of an antigens-binding fragment or of a multispecific antibody of the invention, and two polynucleotides encoding two different light chains: a first light chain pairing specifically with a first VH/CH1 region of said heavy chain; a second light chain pairing specifically with a second VH/CH1 region of said heavy chain and at least one of said light chains being a light chain of a mutated Fab fragment of claim 1. Optionally said host-cell may additionally be transformed with a third polynucleotide encoding a third light chain different from the first and second light chain, and pairing specifically with a third VH/CH1 region of said heavy chain, and eventually with a fourth polynucleotide encoding a fourth light chain different from the first, second, and third light chain, and pairing specifically with a fourth VH/CH1 region of said heavy chain, and possibly with a fifth polynucleotide encoding a fifth light chain different from the first, second, third and fourth light chain, and pairing specifically with a fifth VH/CH1 region of said heavy chain.

Said polynucleotides can be inserted in a same expression vector, or in separate expression vectors.

Host cells which can be used in the context of the present invention can be prokaryotic or eukaryotic cells. Among the eukaryotic cells which can be used, mention will in particular be made of plant cells, cells from yeast, such as Saccharomyces, insect cells, such as Drosophila or Spodoptera cells, and mammalian cells such as HeLa, CHO, 3T3, C127, BHK, COS cells, etc.

The construction of expression vectors of the invention and the transformation of the host cells can be carried out by the conventional techniques of molecular biology.

Still another object of the invention is a method for preparing an antigens-binding fragment or an antibody of the invention. Said method comprises culturing a host-cell of the invention and recovering said antigens-binding fragment or antibody from said culture.

If the protein is secreted by the host-cell, it can be recovered directly from the culture medium; if not, cell lysis will be carried out beforehand. The antibody can then be purified from the culture medium or from the cell lysate, by conventional procedures, known in themselves to those skilled in the art, for example by fractionated precipitation, in particular precipitation with ammonium sulfate, electrophoresis, gel filtration, affinity chromatography, etc.

The multispecific antibodies of the invention can be used in all the applications of multispecific antibodies. In particular they can be used to obtain medicaments useful in a broad range of therapeutic applications. These medicinal products are also part of the object of the invention.

In particular, the multispecific antibodies of the invention can be used for the treatment of various diseases by immunotherapy, including for instance: passive immunotherapy for malignant pathologies, haematological and solid tumors or auto-immune diseases, inflammation, graft rejection, transplantation; active immunotherapy, by modulating interaction between different cell populations in particular immune cells during auto-immune diseases or inflammation; adoptive immunotherapy combining immune cells with multispecific antibody; internalisation of neutralising antibodies into selected intracellular compartment.

By way of non-limitative examples:
  multispecific antibodies of the invention directed against different antigens expressed by a target cells may be used in order to induce its death by apoptosis, its downregulation or conversely its activation;
  multispecific antibodies of the invention directed against antigens expressed on target and effector cells, may be used in order to bridge the two types of cells to induce for instance the killing of the target cells, by the effector cells;
  multispecific antibodies directed against different soluble circulating factors for clearing or blocking at the same time said soluble circulating factors, for instance the simultaneous clearing of VEGF and PDGF in the course of cancer therapy, or the simultaneous clearing (or blocking) of different molecules which inhibits the activity of immunotherapy, such CTLA4, programme cell death 1 (PD1) or TIM3 or BTLA, or in the field of anti-inflammatory therapy, the use of multispecific antibody directed against different inflammatory cytokines, such as Tumor Necrosis Factor (TNF) and Interleukin 1 beta (IL1-β)

The present invention will be understood more clearly from the further description which follows, which refers to non limiting examples of the preparation and properties of a recombinant bi-specific antibody in accordance with the invention.

EXAMPLE 1

Design of an Anti-CD5/Anti-HLA-DR Bi-Specific Antibody

Design of Mutant Fab Fragments

The antibodies chosen for the construction of bi-specific antibodies are an anti-CD5 antibody and an anti-HLA-DR antibody both described in PCT WO 2010/145895.

Under their native form, these antibodies were murine monoclonal antibodies (mAbs), of the IgG2a and IgG1 isotypes, respectively, with kappa light chains. Both mAbs were previously transformed into chimeric mouse/human mAbs with the constant domains of the heavy chain being of human IgG1 subclass and the constant part of the light chains being of kappa type, while the variable domains of both chains remained of mouse origin.

Two different sets of complementary mutations were brought at chosen sites of CH1 and CL chains of the anti-CD5 antibody, the anti-HLA-DR antibody remaining under its native form.

The mutation sites in the anti-CD5 antibody were chosen to be important for CL/CH1 binding, while preserving the most essential residues involved in the proper folding.

The following approaches called "Charged residues" and "Hydrophobicity-polarity-swap" were used.

In the "Charged residues" approach, a pair of interacting polar interface residues was exchanged for a pair of neutral and salt bridge forming residues. The introduction of a salt bridge was hypothesised to reinforce the specificity of the association, whereas an unwanted pairing should be avoided by the lack of sterical and charge complementarity between the wild type and variant chains. After extensive in silico testing the replacement of Thr192 by a Glu on CH1 chain and exchange of Asn137 to a Lys on CL chain were selected. These two mutated residues thin). a salt bridge. Additionally a substitution of Ser114 to Ala on CL chain was made to avoid steric clashes with a bigger lysine side chain. The resulting mutant is designated hereinafter as the "CR3 mutant".

For the "Hydrophobicity-polarity-swap" approach, the modified constant domains were obtained by introducing a quadruple mutation (double mutation on each chain). This modification swaps the nature of two residue-residue interactions on the IgG CH1/CL interface. A pair of interacting apolar residues is exchanged for a pair of polar amino acids, while a pair of interacting polar residues is simultaneously exchanged for a pair of hydrophobic residues. This exchange of the polar/hydrophobic character of the interface interactions was hypothesised to keep the affinity between the mutated CL and CH1 domains unchanged, while decreasing their respective affinity for other wild type counterparts, thus preventing mispairing by virtue of unfavorable interactions occurring upon mismatched (variant/wild type) chains complexation After in silico testing of many potential mutations we chose to replace the Leu143 of the CH1 domain by a Gln residue, while the facing residue of the CL chain, i.e. Val133, was replaced by a Thr residue. This first double mutation constitutes the switch from hydrophobic to polar interactions. Simultaneously a mutation of two interacting serines (Ser188 on CH1 chain and Ser176 on CL chain) to valine residue was selected to perform the switch from polar to hydrophobic interactions. The resulting mutant is designated hereinafter as the "mut4 mutant".

The selected mutations are summarized on Table I below:

TABLE I

| Modifications | CH1 of Heavy chain | CL of Light chain |
| --- | --- | --- |
| Charged residues CR3 mutant | Thr192Glu | Asn137Lys and Ser114Ala |
| Hydrophobicity-polarity swap mut4 mutant | Leu143Gln and Ser188Val | Val133Thr and Ser176Val |

Other mutations were performed using the "knob into holes" approach (RIDGWAY et al., Protein Eng, 9, 617-21, 1996).

These mutations are summarized on Table II below:

TABLE II

| | CH1/Heavy chain | CL/Light chain |
| --- | --- | --- |
| KH1 | Leu124Ala and Leu143Glu | Val133Trp |
| KH2 | Val190Ala | Leu135Trp and Asn137Ala |

The mutated complexes binding free energies were evaluated using the MM-GBSA method. At the same time, the mispaired complexes models were created and their interaction energies were calculated using the same methodology. For the chosen modifications, the complex between the modified CL and CH1 chains was estimated to be as stable as the wild type complex, whereas significantly unfavorable interactions in the mispaired complexes were observed.

Design of a Polypeptide Linker

A polypeptide linker was designed to link the C-terminus of the CH1 region of the anti-HLADR antibody to the N-terminus of the VH region of the mutant anti-CD5 antibody.

This polypeptide linker comprises a full-length IgG1 hinge region, followed by the 9 N-terminal amino-acids of human IgG1 CH2, by a portion of the sequence of human IgA1 hinge, and by the dipeptide GG. It has the following sequence:

EPKSCDKTHTCPPCPAPELLGGPSTPPTPSPSGG (SEQ ID NO: 9)

EXAMPLE 2

Construction of a Recombinant Baculovirus Expressing Anti-HLADR (mAb1) and Anti-CD5 (mAb2) Bi-Specific Antibody The bi-specific antibody has been expressed and produced using the baculovirus/insect cells expression system.

This production required the synthesis of a modified heavy chain comprising the VH/CH1/Hinge domain from a mAb 1 fused to the full length heavy chain of a mAb2 and separated by a linker comprising for example (in our current construct) the lower hinge extended with a peptide derived form the natural hinge of human IgA1+GG.

The two different light chains, one specific of the first antibody and the other one specific of the second antibody are synthesized independently and will be paired to the relevant heavy chains, thanks to the reciprocal mutations introduced into the different CL and CH1 domain as described above.

It could be easier to construct two different baculoviruses the first one expressing the fused-heavy chain and only one light chain and the second one expressing the fused-heavy chain and the second light chain and to co-infect insect cells with the mixture. However, this approach is longer and it would be very difficult to control the stoichiometry of each partner. So we decided to construct only one recombinant virus expressing the fused-heavy chain and the two light chains.

This required the introduction in said baculovirus of two identical sequences for the CL domains, and two identical sequences for the CH1-hinge (CH1+Hg) domains of the heavy chain. This identity may induce a homologous recombination leading to a reorganisation of the genome and to the loss of genetic information.

In order to avoid this phenomenon, we have introduced only one wild type coding sequence, the second one being synthetic (modification of all codons). In this latter, the DNA sequence is different from the original one but encodes a protein identical (100%) to the wild type one.

2.1 Construction of the cDNA Encoding the Fused-heavy Chain

Anti-HLADR Fab+Linker

A synthetic gene encoding the CH1 domain of the anti-HLADR antibody fused to the polypeptide linker of SEQ ID NO: 9 was constructed using hybridization of synthetic overlapping oligonucleotides.

After cloning in a pUC plasmid and control of the sequences, this synthetic gene was introduced, instead of the wild type sequence in the plasmid pOCγ1KCH1SII/LinkerA1PstI/VHanti-HLADR, between the sequence encoding the anti-HLADR VH domain and the sequence encoding the extension peptide described in Example 1 above. The resulting plasmid is named pOCγ1KCH1ϵlinkerA1/VH.

Mutated Anti-CD5 Fab:

In order to ensure the proper pairing between heavy and light chains, mutations CR3, mut4, (KH1 or KH2) were introduced in the CH1 domain of the anti-CD5 Fab moiety. Plasmid pUCCγ1mutT192E (i.e. for CR3 mutant) was digested with NheI/BstXI and the fragment bearing the mutated sequence was purified and inserted in pUCKPSCγ1/VHCD5 digested with NheI/BstXI giving pUCKPSCγ1/VHCD5-CR3.

In the same way, pUCKPSCγ1/VHCD5-mut4, (pUCKPSCγ1/VHCD5-KH1 and pUCKPSCγ1/VHCD5-KH2) were constructed.

Full-length Fused-heavy Chain:

The cDNA encoding the full-length fused-heavy chains were constructed giving pVTanti-HLADR/linkerA1/antiCD5/CR3, pVTanti-HLADR/linkerA1/antiCD5/mut4, (pVTanti-HLADR/linkerA1/antiCD5/KH1, pVTanti-HLADR/linkerA1/antiCD5/KH2) respectively.

The resulting transfer vectors are named pVTanti-HLADR/linkerA1/antiCD5/CR3 and pVTanti-HLADR/linkerA1/antiCD5/mut4 (pVTanti-HLADR/linkerA1/antiCD5/KH1, and pVTanti-HLADR/linkerA1/antiCD5/KH2) respectively.

2.2 Construction of the cDNA Encoding the Light Chain

Construction of a New Transfer Vector

The production of a fully functional bi-specific antibody requires the coexpression of (i) a fused-heavy chain as described above, and of (ii) two light chains, the light chain specific of anti-CD5 bearing the mutations (CR3, mut4, KH1 or KH2) and the light chain of the anti-HLADR (Mab1). This necessitates choosing a third locus, besides the classic polyedrin and p10 loci, to insert a third coding sequence chain into the baculovirus genome. A locus called "gp37" (CHENG et al. J. Gen. Virol., 82, 299-305, 2001) which is not essential for baculovirus replication therefore allowing the insertion of a foreign gene, was chosen.

A new transfer vector (pVTgp37) containing a unique XbaI cloning site under control of a synthetic P10 promoter, flanked by gp37 sequences was constructed.

Construction of a Synthetic CL Domain

As described for the reconstitution of the CH1 domain of the heavy chain, the synthetic CL domain was synthesized using overlapping synthetic oligonucleotides. Two sub-fragments were generated, CKFr1 and CKFr2.

After cloning in a pUC plasmid and control of the sequences, CKFr1 and CKFr2 were introduced, instead of the wild type sequence encoding the Cκ domain, in the plasmid pUCK/VLanti-HLADR Introduction of the Light Chain in the Gp37 Transfer Vector The reconstituted sequence encoding the light chain containing the synthetic constant domain Cκ was isolated after digestion with XbaI and introduced in transfer vector pVTgp37 at the unique XbaI site, giving the final construct pVTgp37P10S1CKεVLanti-HLADR.

2.3 Construction of Recombinant Viruses

Construction of a recombinant virus expressing the bi-specific antibody requires two steps: (i) the construction of a first baculovirus expressing only the light chain of Mab 1, the anti-HLADR (ii) the construction of the virus expressing the bi-specific antibody, anti-CD5/anti-HLADR.

Construction of a Recombinant Virus Expressing the Anti-HLADR

For this purpose, Sf9 cells were cotransfected with pVTgp37P10S1CKεVL/anti-HLADR and with DNA extracted from a modified baculovirus expressing the polyhedrin gene under the control of the gp37 promoter at the gp37 locus.

Recombinant viruses exhibiting a "polyhedrin negative" phenotype were isolated and the genome of four recombinant viruses was controlled by Southern blot using the synthetic kappa c-DNA as a probe. One recombinant virus called BacLC/anti-HLADR was selected.

Construction of Recombinant Viruses Expressing the Bi-specific Antibody

Sf9 cells were cotransfected with transfer vectors bearing the cDNA encoding fused-heavy chains pVTanti-HLADR/linkerA1/anti-CD5 (CR3, mut4, KH1 or KH2) and transfer vectors bearing the cDNA encoding the Mab2 light chains pVTVLIICD5CkmutCR3, pVTVLIICD5Ckmut4, (pVTVLIICD5CkKH1 or pVTVLIICD5CkKH2) in the presence of viral DNA extracted from BacLC/anti-HLADR. Productive clones were screened by ELISA. The genome of recombinant viruses was controlled by Southern blot using cDNAs encoding human constant γ1 and constant κ region respectively as probes. Two of the selected clones (clone C683 for anti-CD5/anti-HLADR(CR3) and clone C977 for anti-CD5/anti-HLADR(mut4) were used for the production of antibodies.

2.4 Production and Purification of the Recombinant Antibodies

Sf9 cells were seeded at a density of 600,000 cells/ml in 400 ml of serum free medium in roller bottles and infected with either clone C683 or clone C977 at a multiplicity of infection of 2 PFU per cell. After 4 days incubation at 28° C., the supernatant was collected and secreted recombinant antibodies were purified on protein A SEPHAROSE chromatography resin (GE, HealthCare). The concentration of purified bi-specific antibodies was determined by using BCA assay, as recommended by the manufacturer PIERCE, and with bovine IgG (ref Standard PIERCE 23209) as a standard.

The structure of the final bi-specific antibodies is shown on FIG. 1.

Legend of FIG. 1: Mab 1: anti-HLA-DR Fab; Mab2: anti-CD5 mutant Fab; Linker: polypeptide linker; Hinge: human IgG1 hinge; Fc human IgG1 Fc region. Due to the presence of 2 cysteine residue(s) from IgG1 hinge the two antigens-binding arms are connected through two interchain disulfide(s) bridge(s).

The molecular weight of the purified anti-CD5/anti-HLADR mutant antibodies was evaluated on SUPEROSE 6chromatography colums (GE HealthCare). More than 90% of the molecules purified on Protein A SEPHAROSE presented an estimated molecular weight of about 299 kDa on SUPEROSE 6, thus correlating with the theoretical molecular weight of 260 kDa (MW calculated without glycans) for the recombinant bi-specific antibody of FIG. 1.

These antibodies were further analysed by SDS-PAGE under reducing or non-reducing conditions. The results are shown on FIG. 2.

Legend of FIG. 2: (A) Samples analyzed in reducing conditions; (B) Samples analyzed in non-reducing conditions; BS: bi-specific antibody; Mab: control IgG1 recombinant anti-HLADR.

The size of the heavy chain of the bi-specific antibodies estimated on this gel corresponds to the calculated molecular weight of 78 000 Da of the fused-heavy chain of the antibody of FIG. 1.

These analyses indicate that the methodology described here leads to the formation of a molecule resulting of the association of two fused-heavy chains with two couples of light chains

EXAMPLE 3

Functional Properties of Anti-CD5/Anti-HLADR (CR3)

Functionality of the Binding Sites

It was important to show that the bi-specific antibodies were able to bind through their 2 different antibody binding sites. To that aim we tested their binding to cells that expressed either CD5 or HLADR by flow cytometry. Briefly all antibodies under study were coupled with phycoerythrin (PE), using the Zenon R-phycoerythrin human (or mouse) IgG labelling kit. Cell lines were then incubated with PE-labelled anti-CD5, anti-HLADR, CR3 bispecific antibodies or control mouse or human IgG1 irrelevant antibodies, washed and then analysed by flow cytometry.

The results of the binding to the CD5$^+$/HLADR$^-$ Jurkat cell line and to the CD5$^-$/HLA-DR$^+$JOK1 cell line are shown on FIGS. 3 and 4, respectively.

Legend of FIG. 3: The Jurkat cell line (CD5+/HLADR−) was stained with PE-labelled mouse anti-CD5 (anti-CD5m), mouse anti-HLADR (anti-HLADRm), bispecific anti-CD5/anti-HLADR CR3 chimeric antibody or control human or mouse IgG1 antibodies (hIgG1 and mIgG1, respectively), all PE-labelled. Cells were then analysed by standard flow cytometry. The overlayed histograms for each antibody are shown, with mean fluorescence intensity values (MFI) indicated in parentheses for each antibody. 1. mIgG-PE 1 μg (MFI=2.6); 2. Anti-CD5m-PE 1 μg (MFI=17); 3. Anti-HLADRm-PE 1 μg (MFI=2.5); 4. hIgG1-PE 1 μg (MFI=3.9); 5. Anti-CD5/anti-HLADR/chi-PE CR3 1 μg (MFI=103).

Legend of FIG. 4: The JOK1 cell line (CD5−/HLADR+) was stained with PE-labelled mouse anti-CD5 (anti-CD5m), mouse anti-HLADR (anti-HLADRm), bispecific anti-CD5/anti-HLADR CR3 chimeric antibody or control human or mouse IgG1 antibodies (mIgG1 and hIgG1, respectively), all PE-labelled. Cells were then analysed by standard flow cytometry. The overlayed histograms for each antibody are shown, with mean fluorescence intensity values (MFI) indicated in parentheses for each antibody. 1. mIgG1-PE 1 μg (MFI=25); 2. (hatched) Anti-CD5m-PE 1 μg (MFI=18); 3. Anti-HLADRm-PE 1 μg (MFI=432); 4. hIgG1-PE 1 μg (MFI=3); 5. Anti-CD5/anti-HLADR/chi-PE CR3 1 μg (MFI=3521).

We conclude that the bi-specific CR3 antibody recognises both specificities (CD5 and HLADR) correctly.

Binding to Antigens Expressed on a Same Cell

Next we wanted to document further that bi-specific CR3 antibody which we showed was able to bind to its 2 targets when they were expressed on the same cell surface, that is in cis. To this aim we first identified a B-CLL patient sample which expressed approximately the same amounts of CD5 and HLADR. B-CLL patients cells were incubated with mouse anti-CD5, mouse anti-HLADR or mouse IgG1 control antibody for 30 minutes a room temperature and then with FITC-labelled anti-mouse IgG secondary antibody. After washing, cells were analysed by standard flow cytometry. As shown in FIG. 5A, the cells expressed similar amounts of CD5 and HLADR, with mean fluorescence intensities of 65 and 98, respectively.

In order to demonstrate that bi-specific anti-CD5/anti-HLADR CR3 antibody bound both antigens on the same cells, we then performed a cross-blocking experiment on the same B-CLL sample. Cells were incubated with 1 μg/ml chimeric CR3 bi-specific antibody, in presence or absence of excess (10 μg/ml) mouse anti-CD5 or mouse anti-HLADR antibodies or both. After washing, binding of bi-specific CR3 antibody was detected by incubation with a secondary monoclonal FITC-labelled antibody (Sigma-Aldrich), specific for human Fc, and unable to bind to mouse Fc (data not shown).

Figure 1:
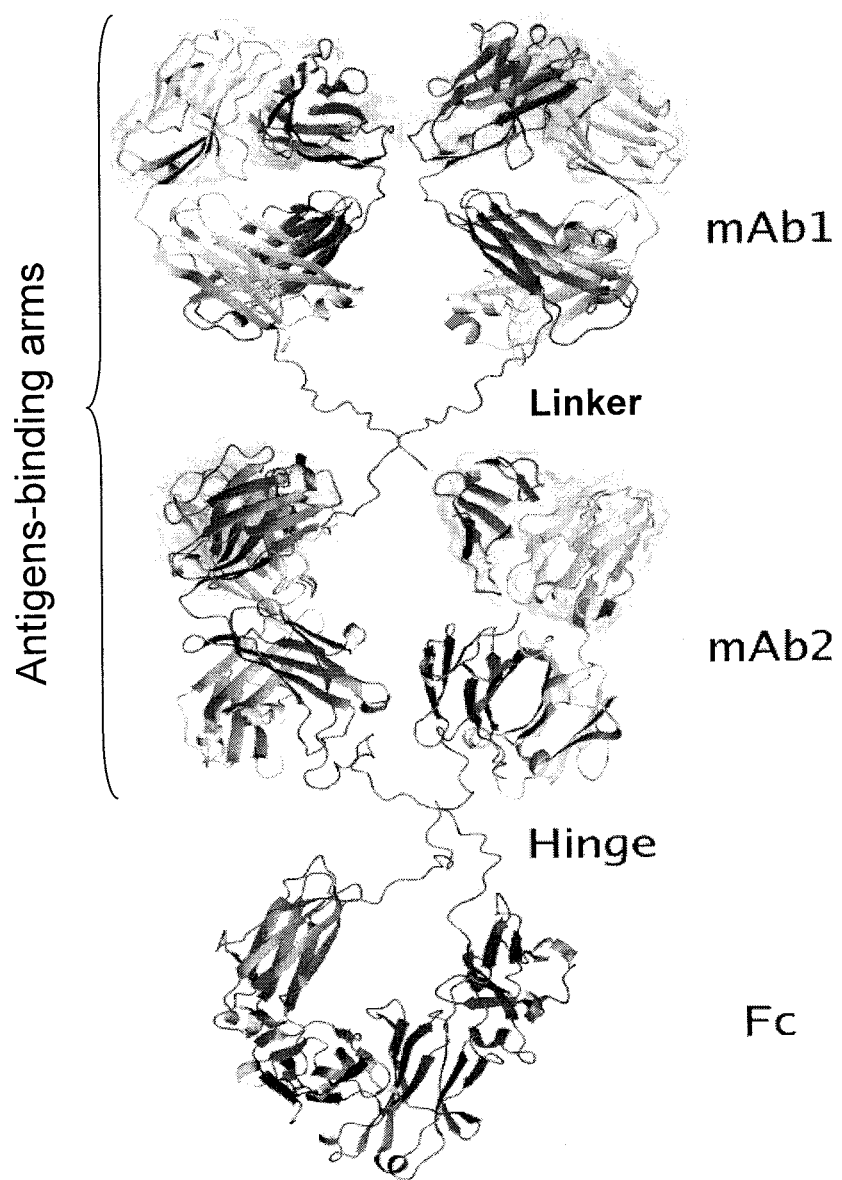
Figure 2:
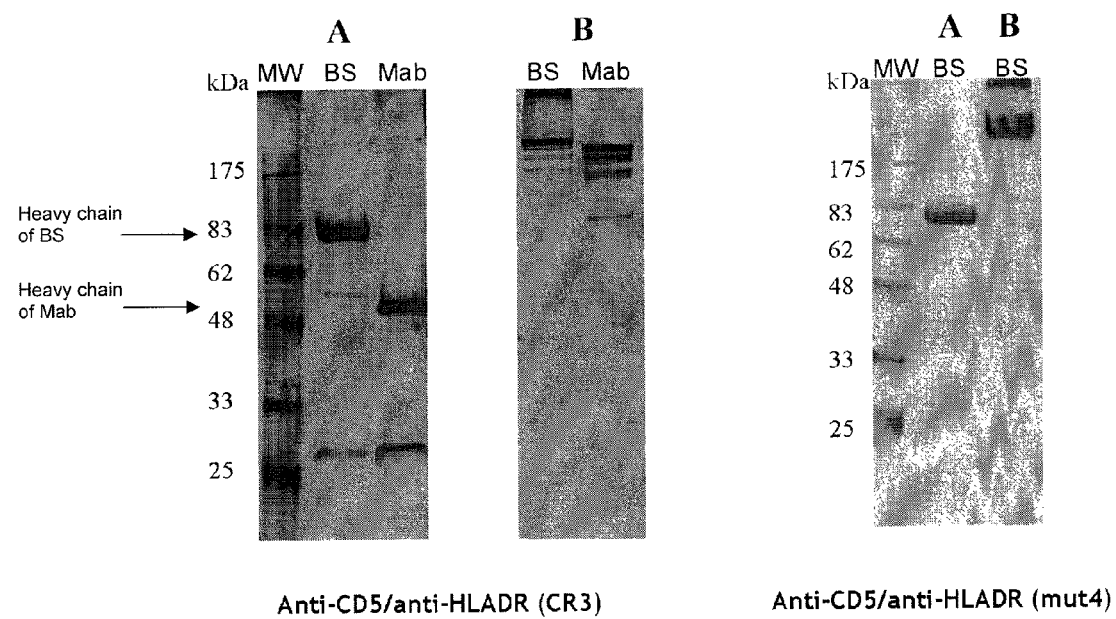
Figure 3:
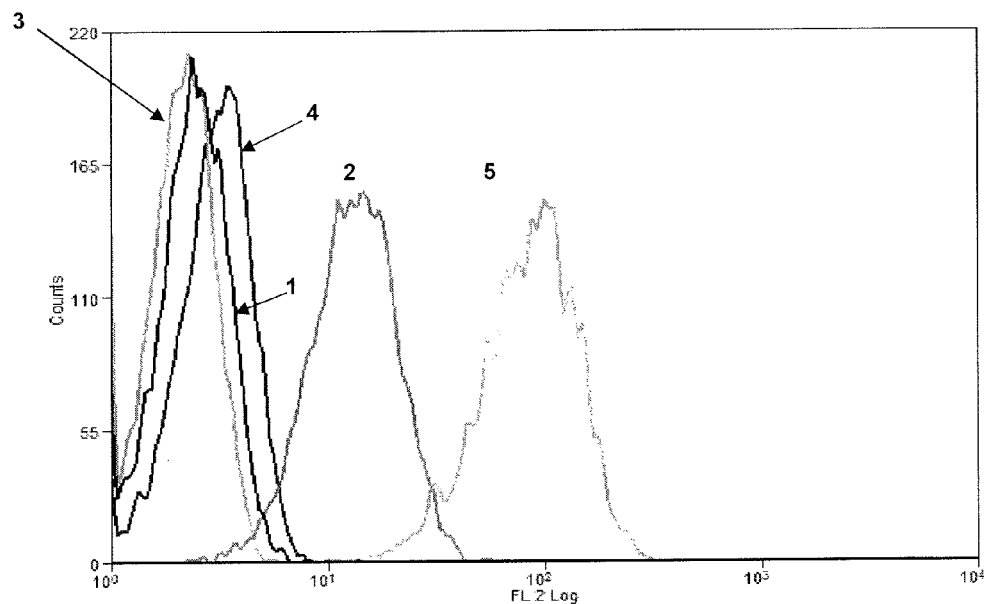
FIG. 3 shows that both mouse anti-CD5 and bi-specific CR3 are able to bind to the CD5+ Jurkat cell line, whereas anti-HLADR antibody does not, as expected. Thus bi-specific CR3 antibody recognises the CD5 antigen on CD5 positive cell line.
Figure 4:
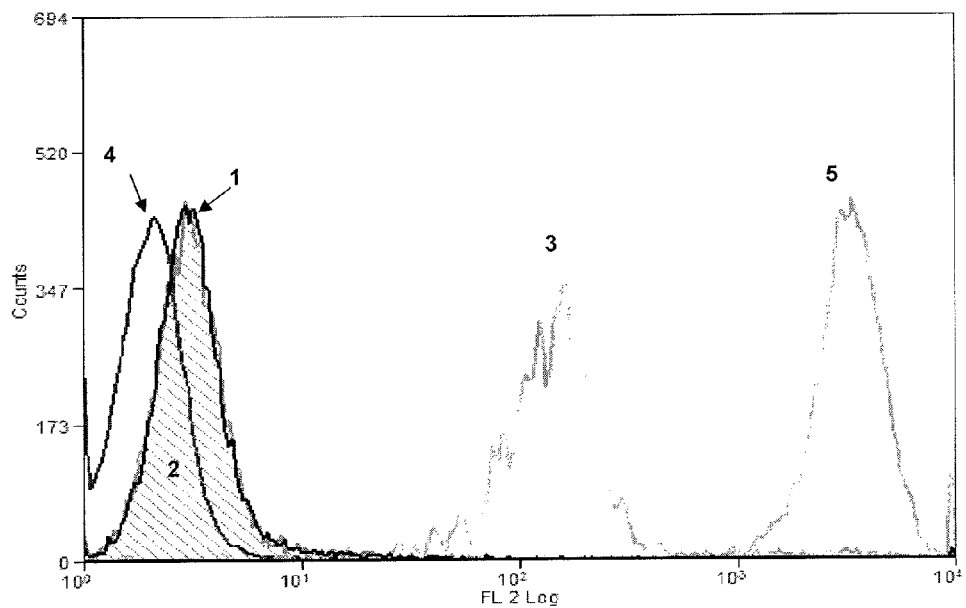
FIG. 4 shows that mouse anti-HLADR and bi-specific CR3 antibodies bind with high intensity to the CD5−/HLADR+ JOK cell line, whereas mouse anti-CD5 does not, as expected. This demonstrates that the bi-specific CR3 antibody recognises the HLADR antigen on a HLADR+ cell line.
Figure 5:
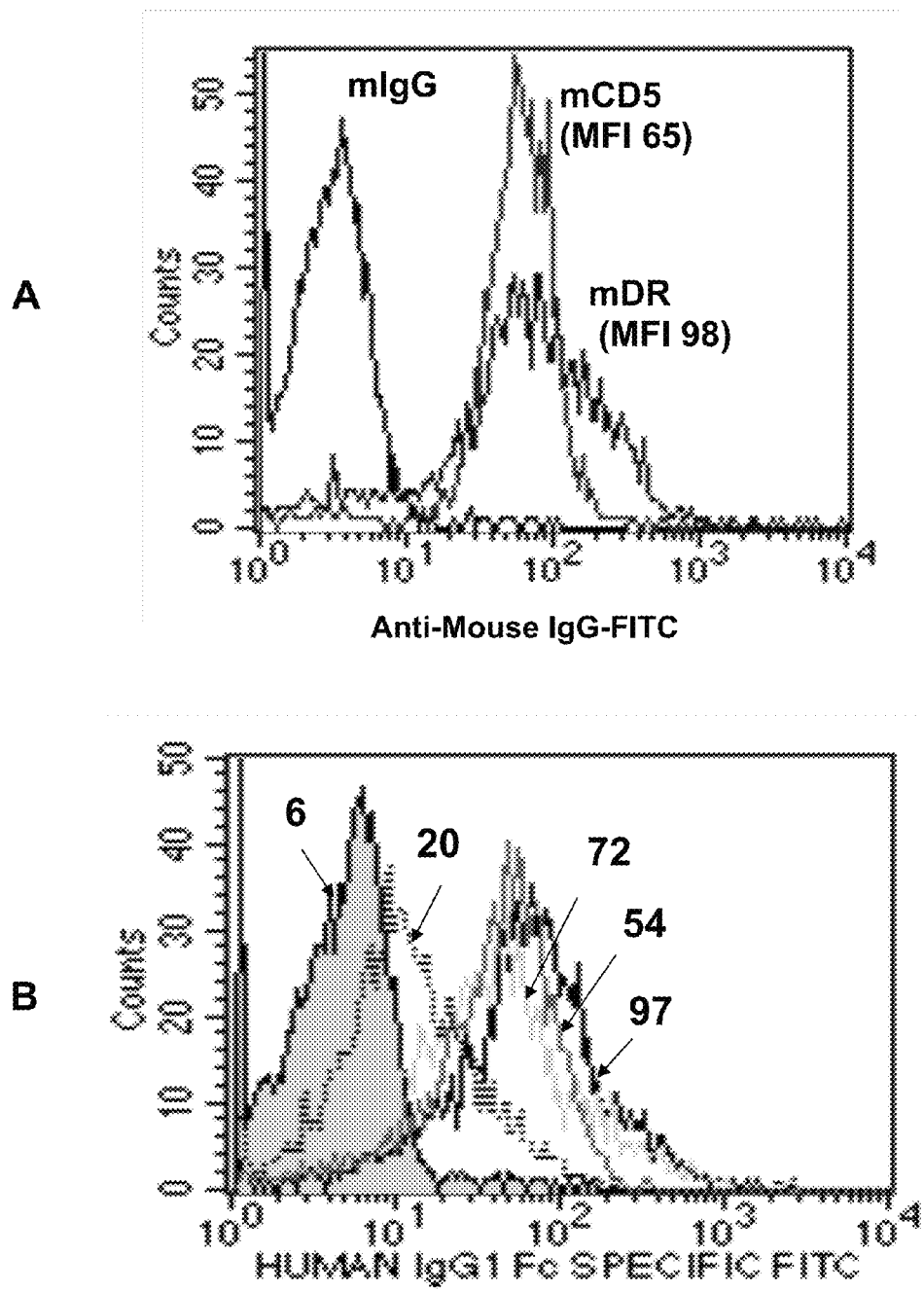

Legend of FIG. 5:

Panel A: B-CLL patient cells were incubated with mouse anti-CD5 (mCD5), mouse anti-HLADR (mDR) or mouse irrelevant IgG antibody (mIgG) as control. After washing, cells were stained with FITC-labelled anti-mouse secondary antibody and then analysed by standard flow cytometry. The MFI for mCD5 and mDR are indicated between brackets.

Panel B: Cells from the same patient as in A were incubated with 1 μg/ml chimeric CR3 alone (dark thick line) or in presence of 10 μg/ml mouse anti-CD5 (light grey line) or mouse anti-HLADR (dark grey line) or both (discontinuous line). After washing, cells were incubated with monoclonal FITC-labelled anti human Fc antibody, washed and analysed by flow cytometry. The overlayed histograms for each condition are shown with MFI obtained in each case indicated above each curve. BS: Bi-specific, m: mouse, h: human, chi: chimeric.

|  |  | MFI |
|---|---|---|
|  | Negative control (anti-human IgG-FITC) | 6 |
|  | chBI-CR3 1 ug/ml | 97 |
|  | chBI-CR3 1 ug/ml + mCD5 10 ug/ml | 72 |
|  | chBI-CR3 1 ug/ml + mDR 10 ug/ml | 54 |
|  | chBI-CR3 1 ug/ml + mCD5 + mDR 10 ug/ml | 20 |

As shown in FIG. 5B, bi-specific CR3 antibody alone resulted in a mean fluorescence intensity (MFI) of 97. Competition by anti-CD5 or anti-HLADR alone only partially displaced CR3 (MFI 72 and 54, respectively). In contrast, adding both antibodies together displaced bi-specific CR3 antibody nearly completely (MFI 20). These data suggest that bi-specific CR3 antibody binds to the cells via either the CD5 or HLADR moiety and displacing it requires competition by a mixture of anti-CD5 and anti-HLADR antibodies.

We conclude from these data that the bi-specific antibody CR3, the chimeric anti-CD5/anti-HLADR antibody can bind to both HLADR and CD5 on the same cell.

EXAMPLE 4

Functionality of the Fc Moiety and of the Antigens-Binding Moiety of the Bi-Specific Antibodies Fc Moiety The Fc moiety of antibody molecules are capable of activating various immune functions such as phagocytosis (ADP) and antibody dependent cytotoxicity (ADCC) by binding to FcγRs on macrophages (FcγRI, II and III) and NK cells (FcγRIII), respectively. Since the constructed bi-specific antibodies have an Fc moiety derived from human IgG1, we have tested whether it is functional and therefore able to mediate these immune mediated functions.

Antibody-Dependent Cellular Cytotoxicity (ADCC) by Natural Killer Cells

First we wanted to determine whether the Fc part of the bi-specific CR3 molecule was active when either of its paratopes was binding to its respective molecule. We analyzed the ADCC, mediated by Fc binding to NK cells, induced on a CD5+/HLA-DR− target such as Jurkat cells and on HLA-DR+/CD5− targets such as JOK1 and double positive targets JOK1.5.3 cells. NK cells were purified from peripheral blood mononuclear cells by immunobead selection. Target cells were labelled with 1 μM carboxyfluorescein diacetate succinimidyl ester (CFSE) at 4° C. for 20 minutes, washed and cultured with purified NK cells at 37° C. for 4 hours at a 10:1 effector to target ratio (E:T). Cells were then labelled with 7AAD and analysed by flow cytometry. Percentage killing was measured as percent 7AAD positive targets (CFSE+) with respect to total CFSE+ cells.

Figure 6:
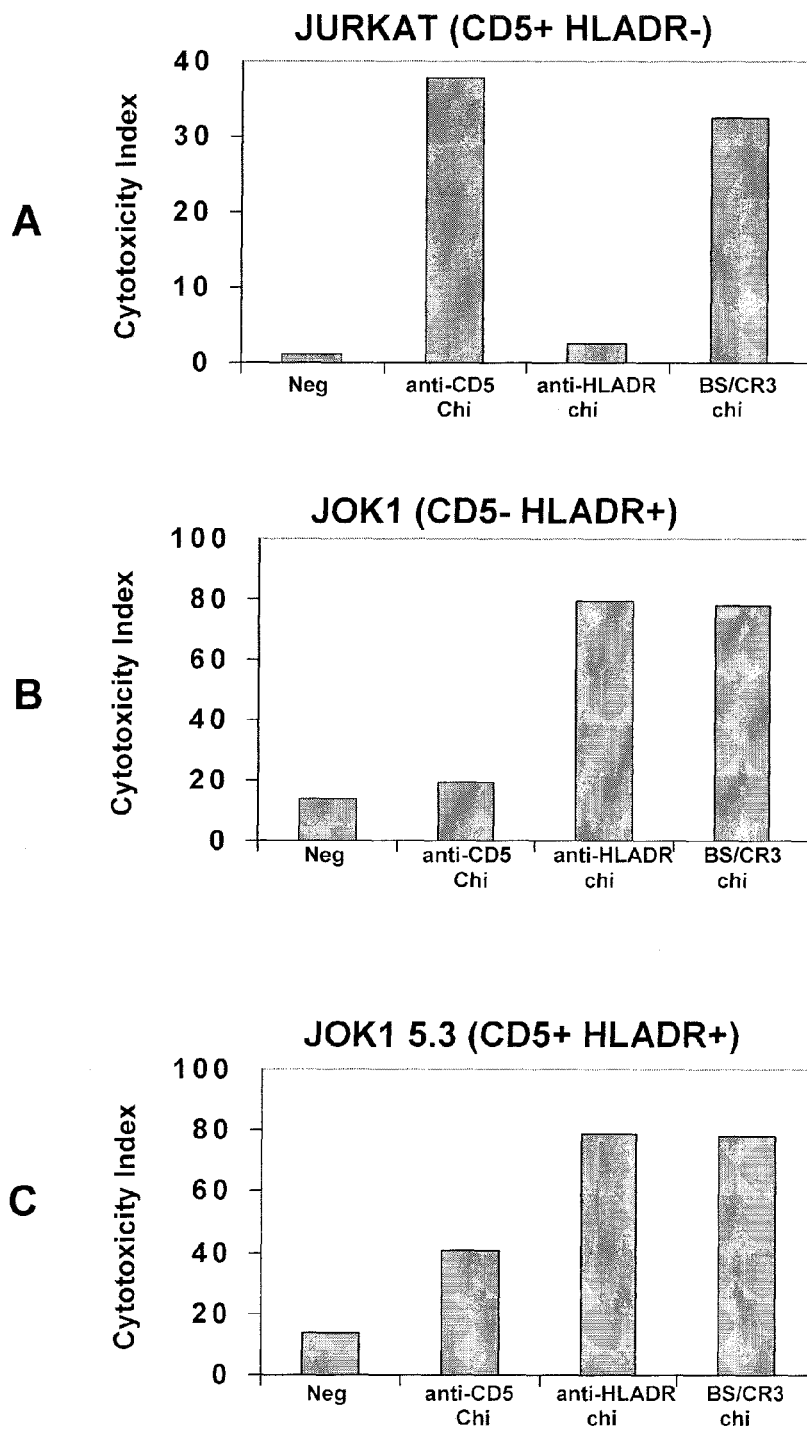

The results are shown in FIG. 6.

Legend of FIG. 6: JURKAT (CD5+HLADR−, panel A), JOK1 (CD5−HLADR+, panel B) and JOK1 5.3 (CD5+HLADR+, panel C) were CFSE labelled and used in ADCC assays in presence of human NK cells at 10:1 E:T ratio and 1 μg/ml chimeric anti-CD5 (anti-CD5chi) or chimeric anti-HLADR (anti-HLADRchi) or 2 μg/ml bi-specific CR3 antibody. Cytotoxicity was measured by flow cytometry after 4 hours at 37° C.

The data show that the bi-specific CR3 antibody mediates ADCC on all 3 cell lines (33-78% cytotoxicity). In contrast anti-CD5chi and anti-HLADRchi are cytotoxic only for CD5$^+$ or HLADR$^+$ cell lines, respectively.

We conclude that the Fc moiety of bi-specific CR3 antibody is functional allowing the antibody to mediate ADCC of targets expressing either CD5, HLADR or both antigens.

Phagocytosis

In order to confirm the functionality of Fc part of CR3 molecule with respect to binding to FcγRs present on macrophages (FcγRI, FcγRII and FcγRIII), and simultaneous binding of its paratopes to their respective molecules, we assessed ADP in vitro. CD 14$^+$ monocytes were purified from healthy donors' mononuclear cells by anti-CD14 microbeads magnetic cell sorting, according to the manufacturer's instructions (Miltenyi Biotec). They were cultured in 8-well chamber slides (LabTek; Nunc) at $2 \times 10^5$/well for 6-7 days in RPMI 1640 medium supplemented with 20% foetal bovine serum and 20 ng/ml human rM-CSF (R&D Systems). Phagocytosis of B-CLL target cells (CD5$^+$/HLA-DR$^+$) by these macrophages was then performed. A total of $2 \times 10^5$ B-CLL targets was added in each well in presence or absence of 0.01 to 0.1 μg/ml CR3 bi-specific antibody or anti-CD20 mAb rituximab. After 2 h at 37° C., slides were gently rinsed in PBS, fixed, and stained with May-Gruenwald Giemsa. Phagocytosis was evaluated by counting under the microscope at least 200 cells for each experimental condition, using the ImageJ 1.38 image processing and analysis software, and calculating the percentage of macrophages that engulfed at least one tumor target cell with respect to total macrophages.

Figure 7:
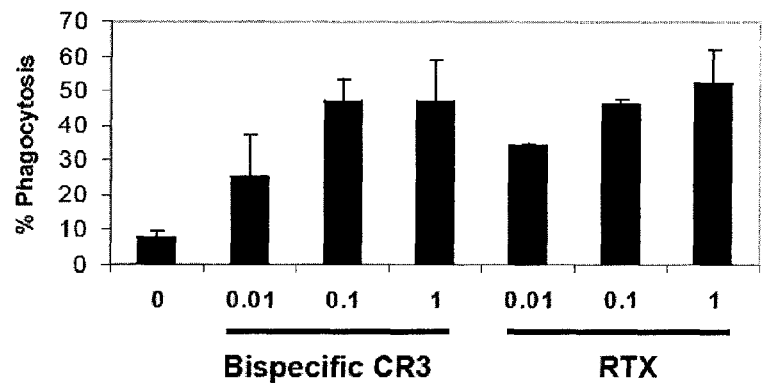

The results are shown on FIG. 7.

Legend of FIG. 7: Percentage phagocytosis is shown in the Y-axis and the concentrations of antibody used are shown in the X-axis, ranging from 0.01 to 1 μg/ml of bi-specific antibody CR3 or monospecific anti-CD20 antibody rituximab (RTX). 0: no antibody added.

The data below show that the bi-specific CR3 antibody mediates about 40% phagocytosis above background at 0.1-1 μg/ml, similarly to Rituximab. Negative control antibody trastuzumab (anti-HER2) does not mediate phagocytosis (data not shown).

Thus we conclude that the Fc moiety of bi-specific CR3 antibody molecule is functional and can mediate phagocytosis of target cells by macrophages through interaction of Fc with FcγRs on these cells.

Antigens-binding Moiety

Redirected by Cytokine Induced Killer Cells by Bi-Specific CR3 Antibody

We then determined whether the paratopes of bi-specific CR3 antibody can bind to its target antigens present on 2 different cell types.

Cytokine induced killer cells (CIK) are activated CD3$^+$ CD56$^+$ double positive T lymphocytes generated in vitro by stimulation of peripheral blood mononuclear cells with interferon-gamma, anti-CD3 and expansion in vitro for 3-4 weeks with interleukin-2 (SCHMIDT WOLFF et al. J. Exp. Med. 174:139-149; 1991) CIK cells have significant natural cytotoxic activity against tumor but not normal cells in vitro, similarly to NK cells. CIK cells however do not express FcγR and therefore do not mediate ADCC in presence of mono-specific IgG antibodies such as rituximab. CIK cells express CD5. For this reason CIK cells can be redirected towards HLADR positive but not negative tumor cells by bi-specific antibody CR3 which recognizes CD5 on CIK and HLA-DR on tumor target. Differently from ADCC, this redirected killing uses the two Fab specificities of the antibody and not the Fc portion.

Method

Peripheral blood mononuclear cells were cultured at $3 \times 10^6$/ml in serum-free hematopoietic cell medium X-VIVO 15 medium (BioWhittaker, Walkersville, Md., USA) with 1000 U/mL IFN-γ (Gammakine; Boehringer Ingelheim, Vienna, Austria) added on day 0.50 ng/mL anti-CD3 (OKT-3, Janssen-Cilag S.p.a., Italy) added on day 1 and 500 U/mL rhIL-2 included in the medium from day 1 onwards. Expansion was performed for 21-28 days adjusting cells to $1 \times 10^6$/ml in fresh rhIL-2 containing medium every 3-4 days. At the end of the expansion, CD3$^+$/CD5$^+$/CD56$^+$ cytotoxic CIK cells were 40-70% of the population. Remaining cells are mostly CD3$^+$/CD56$^-$ CIK precursor cells.

The human tumor target cell lines BJAB (CD5$^-$/HLA-DR$^+$), JOK1.5.3 (CD5$^+$/HLA-DR$^+$), Jurkat (CD5$^+$/HLA-DR$^-$) and KCL22 (CD5$^-$/HLA-DR$^-$) were maintained in RPMI-1640 medium (Lonza, Basel, Switzerland) supplemented with 10% foetal bovine serum (Euroclone, Wetherby, West Yorkshire, U.K.), 2 mM L-glutamine (Euroclone) and 110 μM gentamycin (PHT Pharma, Milano, Italy).

For redirected cytotoxicity assays, target cell lines were labelled for 30 minutes at 37° C. with 3.5 μM Calcein-AM (Fluka, Sigma-Aldrich Company, Ayrshire, UK). After washing labelled target cells were distributed in 96-well plates at $5 \times 10^3$/well. CIK cell were added at a 10:1 effector to target ratios in presence or absence of 1 μg/ml bi-specific CR3 antibody. After 4 hours, the cells were sedimented by centrifugation, 100 μl supernatant were collected and calcein release was determined using a fluorescence microplate reader (GENios, TECAN, Austria GmbH, Salzburg, Austria) with excitation at 485 nm and emission at 535 nm. The percentage (%) specific lysis was calculated as: (test calcein release−spontaneous calcein release)×100/(maximal calcein release−spontaneous calcein release). Maximal lysis was achieved by adding 1% Triton X-100 (a nonionic surfactant).

Figure 8:
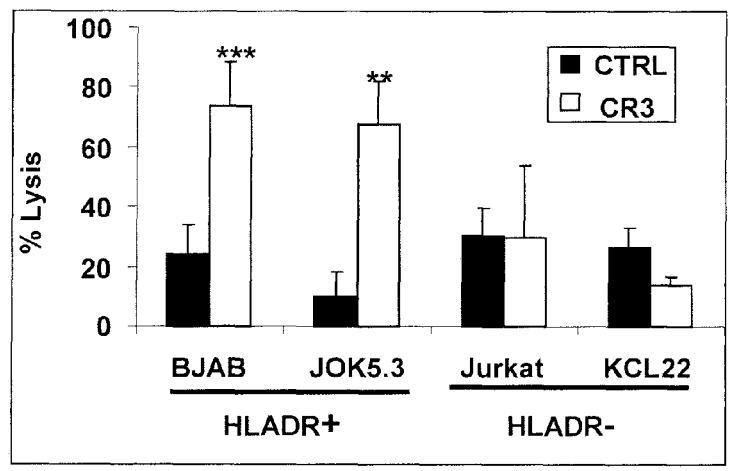

The results are shown on FIG. 8.

Legend of FIG. 8: Calcein-AM loaded target cell lines BJAB, JOK1.5.3, Jurkat and KCL22 were incubated in presence (open bars) or absence (black bars) of 1 μg/ml bi-specific CR3 antibody and in presence of CIK cells at a 10:1 effector:target ratio. After 4 hours, supernatants were collected and released calcein measured. The data show the measured percentage lysis (Y-axis) as means and standard deviations of 2-6 separate experiments with each cell line. CTRL: Control without antibody.

The results show that in vitro, percentage killing (lysis) of HLADR positive (BJAB, JOK15.3), but not HLADR negative targets (Jurkat, KCL22), is increased by 50-60% by addition of 1 μg/ml CR3 antibody in presence of CIK cells at a 10:1 effector:target ratio. This demonstrates that the intercellular bridge formed by the bi-specific CR3 antibody dramatically enhances killing of the HLADR$^+$ targets by CIK cells. No enhancement of killing of HLADR negative targets is observed, demonstrating specificity.

The specificity of the enhancement by the bi-specific CR3 antibody of the cytotoxic effect of CIK cells with respect to normal T cells was further demonstrated as follows: HLADR$^+$ BJAB target cells were incubated with different amounts of peripheral blood mononuclear cells as effector cells at effector:target ratios ranging form 1:1 to 10:1 in presence or absence of 1 µg/ml CR3. Lysis was measured at 4 hours.

Figure 9:
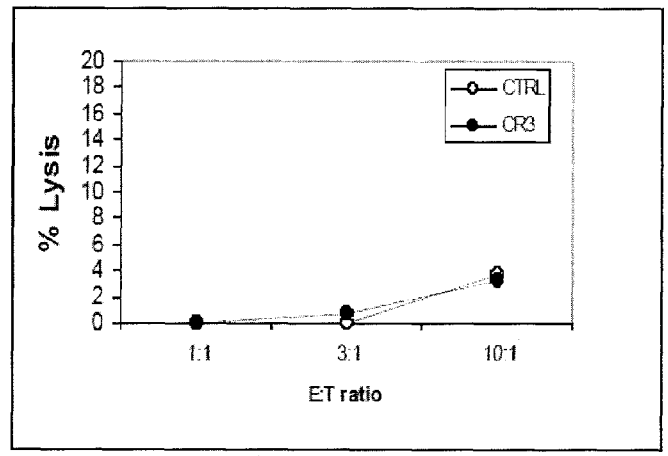

The results are shown on FIG. 9.

Legend of FIG. 9: Cytotoxicity experiments were performed with PBMC as effectors and BJAB as target cells at different effector:target ratios, in presence (black circles) and absence (open circles) of bi-specific antibody CR3. X-axis: Effector:target ratio; Y-axis percent of lysis; CR3: bi-specific CR3 antibody; CTRL: control without antibody.

No effect of the CR3 antibody on lysis of the HLADR$^+$ targets by normal T is observed.

These results show that the divalent bi-specific antibody CR3 can be used in conjunction with cytokine induced killer (CIK) cells in adoptive immunotherapy treatment. In this case the different specificities of the 2 Fab pairs are used, one pair (in this case anti-HLADR) recognizing target cell and the other (anti-CD5) the effector CIK cells. These results indicate that different target antigens could be inserted such as HER1, HER2, EpCAM, CD19, CD20 or others, in place of HLADR. The results also indicate that other antigens expressed by effector cells could be used in place of CD5, such as CD3 expressed by T lymphocytes, FcγRIII or NKG2D present on NK cells or FcγRI-III on macrophages in the frame work of different forms of cancer therapy.

Redirected Killing by Cytokine Induced Killer Cells by Bi-Specific MUT 4 Antibody We determined whether the bi-specific MUT 4 antibody can bind to its target antigens present on 2 different cell types and redirect the killing of CD5+cytokine induced killer cells (CIK) towards a HLADR+ lymphoma target (JOK1 5.3). CIK are activated CD3$^+$CD56$^+$ double positive T lymphocytes generated in vitro by stimulation of peripheral blood mononuclear cells with interferon-gamma, anti-CD3 and expansion in vitro for 3-4 weeks with interleukin-2 (SCHMIDT WOLFF et al. J. Exp. Med. 174:139-149; 1991) CIK cells have significant natural cytotoxic activity against tumor but not normal cells in vitro, similarly to NK cells. CIK cells however do not express FcγR and therefore do not mediate ADCC in presence of mono-specific IgG antibodies such as rituximab. CIK cells express CD5. For this reason CIK cells can be redirected towards HLADR positive but not negative tumor cells by bi-specific antibody MUT 4 which recognizes CD5 on CIK and HLADR on tumor target. Differently from ADCC, this redirected killing uses the two Fab specificities of the antibody and not the Fc portion.

Method

Peripheral blood mononuclear cells were cultured at 3×10$^6$/ml in serum-free X-VIVO 15 medium (a cell medium from BioWhittaker, Walkersville, Md., USA) with 1000 U/mL IFN-γ (Gammakine; Boehringer Ingelheim, Vienna, Austria) added on day 0.50 ng/mL anti-CD3 (OKT-3, Janssen-Cilag S.p.a., Italy) added on day 1 and 500 U/mL rhIL-2 included in the medium from day 1 onwards. Expansion was performed for 21-28 days adjusting cells to 1×10$^6$/ml in fresh rhIL-2 containing medium every 3-4 days and. At the end of the expansion, CD3$^+$/CD5$^+$/CD56$^+$ cytotoxic CIK cells were about 50% of the population. Remaining cells are mostly CD3$^+$/CD56$^-$ CIK precursor cells.

The human tumor target cell line JOK1.5.3 (CD5$^+$/HLADR$^+$) was maintained in RPMI-1640 medium (Lonza, Basel, Switzerland) supplemented with 10% foetal bovine serum (Euroclone, Wetherby, West Yorkshire, U.K.), 2 mM L-glutamine (Euroclone) and 110 µM gentamycin (PHT Pharma, Milano, Italy).

For redirected cytotoxicity assays, target cell lines were labelled for 30 minutes at 37° C. with 3.5 µM Calcein-AM (Fluka, Sigma-Aldrich Company, Ayrshire, UK). After washing labelled target cells were distributed in 96-well plates at 5×10$^3$/well. CIK cell were added at a 10:1 effector to target ratios in presence or absence of 1 or 5 µg/ml bi-specific MUT 4 antibody, CR3 antibody or rituximab (RTX) as controls. After 4 hours, the cells were sedimented by centrifugation, 100 µl supernatant were collected and calcein release was determined using a fluorescence microplate reader (GENios, TECAN, Austria GmbH, Salzburg, Austria) with excitation at 485 nm and emission at 535 nm. The percentage (%) specific lysis was calculated as: (test calcein release−spontaneous calcein release)×100/(maximal calcein release−spontaneous calcein release). Maximal lysis was achieved by adding 1% TRITON X-100.

Figure 10:
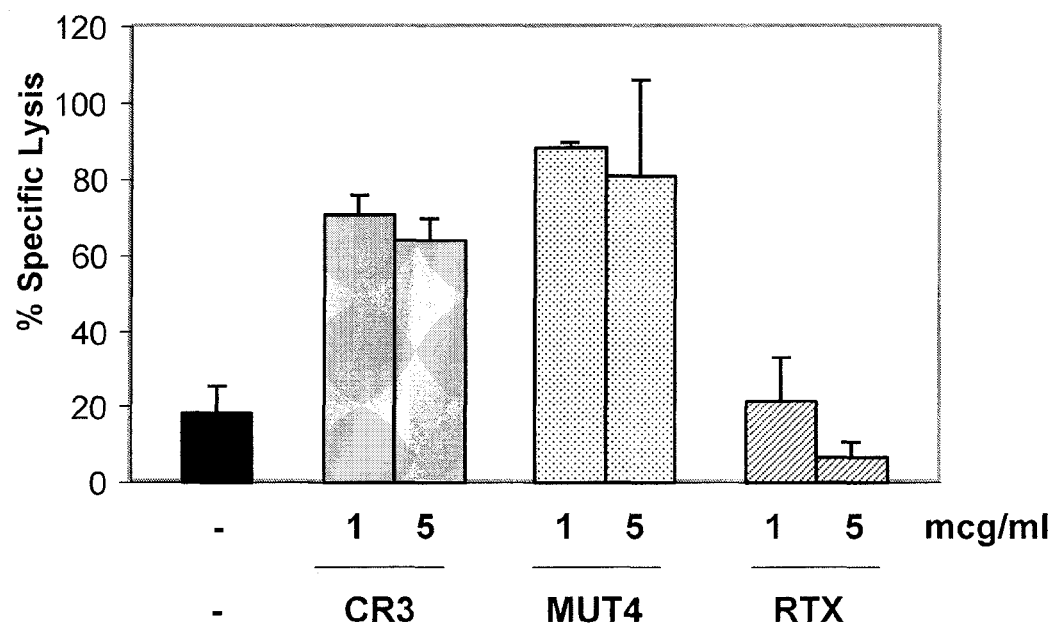

The results are shown on FIG. 10.

Legend of FIG. 10: Calcein-AM loaded target cells JOK1.5.3 were incubated in presence or absence of 1 or 5 µg/ml bi-specific MUT 4, CR3 or rituximab (RTX) antibodies and in presence of CIK cells at a 10:1 effector:target ratio. After 4 hours, supernatants were collected and released calcein measured. The data show the measured percentage lysis (Y-axis) as means and standard deviations of 2 independent experiments. −: control without antibody.

The results show that in vitro, percentage killing (lysis) of HLADR positive JOK15.3 is increased by 60-70% by addition of 1-5 µg/ml MUT 4 antibody and by 40-50% by addition of CR3 antibody, in presence of CIK cells at a 10:1 effector:target ratio. Rituximab in contrast has no significant effect. This demonstrates that the intercellular bridge formed by the bi-specific MUT 4 antibody dramatically enhances killing of the HLADR$^+$ targets by CIK cells, similar or higher to that obtained with CR3.

The invention claimed is:

1. An isolated multispecific antigens-binding fragment comprising at least two Fab fragments with different CH1 and CL domains, wherein said Fab fragments comprise:
   a. a wild-type Fab fragment consisting of wild-type human CH1 and wild-type human CL domains of an immunoglobulin, and the VH and VL domains of an antibody recognizing an epitope of interest; and
   b. a mutated Fab fragment consisting of:
      i. the VH and VL domains of an antibody recognizing an epitope of interest;
      ii. a CH1 domain of a human immunoglobulin comprising substitution of the threonine residue at position 192 of said CH1 domain with a glutamic acid residue ; and
      iii. a CL-kappa domain of a human immunoglobulin comprising substitution of the asparagine residue at position 137 of said CL domain with a lysine residue and substitution of the serine residue at position 114 of said CL domain with an alanine residue,
   wherein the sequence position numbers used for the CH1 and CL domains refer to Kabat numbering and each Fab fragment recognizes a different epitope of interest, and said Fab fragments are tandemly arranged in any order, the C-terminal end of the CH1 domain of the first Fab fragment being linked to the N-terminal end of the VH domain of the following Fab fragment through a polypeptide linker.

2. The isolated multispecific antigens-binding fragment of claim 1, wherein the polypeptide linker has a length of at least 20 amino acids.

3. The isolated multispecific antigens-binding fragment of claim 1, wherein the polypeptide linker comprises all or part of the sequence of the hinge region of one or more immunoglobulin(s) selected from the group consisting of: IgA, IgG, and IgD.

4. The isolated multispecific antigens-binding fragment of claim 1, wherein the polypeptide linker has the sequence of SEQ ID NO: 9.

5. An isolated multispecific antibody having two identical antigens-binding arms, each consisting of an antigens-binding fragment of claim 1.

6. The isolated multispecific antibody of claim 5, which has an immunoglobulin-like structure, comprising:
   a. two identical antigens-binding arms each consisting of an antigens-binding fragment of any of claims 1 to 4;
   b. the dimerized CH2 domains and CH3 domains of an immunoglobulin; and
   c. the hinge region of an IgA, IgG, or IgD, linking the C-terminal ends of the CH1 domains of the antigens-binding arms to the N-terminal ends of the CH2 domains.

7. A therapeutic composition comprising: a. a multispecific antigens-binding fragment of claim 1 and a pharmaceutically acceptable vehicle, or b. a multispecific antibody of claim 5, and a pharmaceutically acceptable vehicle.

* * * * *

SEQUENCE LISTING

<160> NUMBER OF SEQ ID NOS: 14

<210> SEQ ID NO 1
<211> LENGTH: 19
<212> TYPE: PRT
<213> ORGANISM: Homo sapiens

<400> SEQUENCE: 1

Val Pro Ser Thr Pro Pro Thr Pro Ser Pro Ser Thr Pro Pro Thr Pro
1               5                   10                  15

Ser Pro Ser

-continued

<210> SEQ ID NO 2
<211> LENGTH: 6
<212> TYPE: PRT
<213> ORGANISM: Homo sapiens

<400> SEQUENCE: 2

Val Pro Pro Pro Pro Pro
1               5

<210> SEQ ID NO 3
<211> LENGTH: 58
<212> TYPE: PRT
<213> ORGANISM: Homo sapiens

<400> SEQUENCE: 3

Glu Ser Pro Lys Ala Gln Ala Ser Ser Val Pro Thr Ala Gln Pro Gln
1               5                   10                  15

Ala Glu Gly Ser Leu Ala Lys Ala Thr Thr Ala Pro Ala Thr Thr Arg
                20                  25                  30

Asn Thr Gly Arg Gly Gly Glu Glu Lys Lys Glu Lys Glu Lys Glu
            35                  40                  45

Glu Gln Glu Glu Arg Glu Thr Lys Thr Pro
    50                  55

<210> SEQ ID NO 4
<211> LENGTH: 15
<212> TYPE: PRT
<213> ORGANISM: Homo sapiens

<400> SEQUENCE: 4

Glu Pro Lys Ser Cys Asp Lys Thr His Thr Cys Pro Pro Cys Pro
1               5                   10                  15

<210> SEQ ID NO 5
<211> LENGTH: 15
<212> TYPE: PRT
<213> ORGANISM: Homo sapiens

<400> SEQUENCE: 5

Glu Pro Lys Ser Cys Asp Lys Thr His Thr Cys Pro Pro Cys Pro
1               5                   10                  15

<210> SEQ ID NO 6
<211> LENGTH: 17
<212> TYPE: PRT
<213> ORGANISM: Homo sapiens

<400> SEQUENCE: 6

Glu Leu Lys Thr Pro Leu Gly Asp Thr Thr His Thr Cys Pro Arg Cys
1               5                   10                  15

Pro

<210> SEQ ID NO 7
<211> LENGTH: 15
<212> TYPE: PRT
<213> ORGANISM: Homo sapiens

<400> SEQUENCE: 7

Glu Pro Lys Ser Cys Asp Thr Pro Pro Pro Cys Pro Arg Cys Pro
1               5                   10                  15

<210> SEQ ID NO 8
<211> LENGTH: 12

```
<212> TYPE: PRT
<213> ORGANISM: Homo sapiens

<400> SEQUENCE: 8

Glu Ser Lys Tyr Gly Pro Pro Cys Pro Ser Cys Pro
1               5                   10

<210> SEQ ID NO 9
<211> LENGTH: 34
<212> TYPE: PRT
<213> ORGANISM: Artificial
<220> FEATURE:
<223> OTHER INFORMATION: Polypeptide linker

<400> SEQUENCE: 9

Glu Pro Lys Ser Cys Asp Lys Thr His Thr Cys Pro Pro Cys Pro Ala
1               5                   10                  15

Pro Glu Leu Leu Gly Gly Pro Ser Thr Pro Pro Thr Pro Ser Pro Ser
                20                  25                  30

Gly Gly

<210> SEQ ID NO 10
<211> LENGTH: 9
<212> TYPE: PRT
<213> ORGANISM: Homo sapiens

<400> SEQUENCE: 10

Ala Pro Glu Leu Leu Gly Gly Pro Ser
1               5

<210> SEQ ID NO 11
<211> LENGTH: 8
<212> TYPE: PRT
<213> ORGANISM: Homo sapiens

<400> SEQUENCE: 11

Thr Pro Pro Thr Pro Ser Pro Ser
1               5

<210> SEQ ID NO 12
<211> LENGTH: 32
<212> TYPE: PRT
<213> ORGANISM: Artificial
<220> FEATURE:
<223> OTHER INFORMATION: Polypeptide linker

<400> SEQUENCE: 12

Glu Pro Lys Ser Cys Asp Lys Thr His Thr Cys Pro Pro Cys Pro Ala
1               5                   10                  15

Pro Glu Leu Leu Pro Ser Thr Pro Pro Thr Pro Ser Pro Ser Thr Pro Gly Gly
                20                  25                  30

<210> SEQ ID NO 13
<211> LENGTH: 5
<212> TYPE: PRT
<213> ORGANISM: Homo sapiens

<400> SEQUENCE: 13

Ala Pro Glu Leu Leu
1               5

<210> SEQ ID NO 14
<211> LENGTH: 10
<212> TYPE: PRT
```

```
<213> ORGANISM: Artificial
<220> FEATURE:
<223> OTHER INFORMATION: Linker fragment

<400> SEQUENCE: 14

Pro Ser Thr Pro Pro Ser Pro Ser Thr Pro
1               5                   10
```